(12) United States Patent
Carr et al.

(10) Patent No.: US 6,846,298 B1
(45) Date of Patent: Jan. 25, 2005

(54) BLOOD PRODUCT DELIVERY SYSTEM

(75) Inventors: Raymond A. Carr, Largo, FL (US); Michael J. Amery, Skillman, NJ (US); Niels Erik Holm, Birkerød (DK)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/122,284

(22) Filed: Jul. 24, 1998

Related U.S. Application Data

(60) Provisional application No. 60/053,746, filed on Jul. 25, 1997.

(51) Int. Cl.[7] .................. A61M 37/00; A61M 5/00; A61B 19/00; G06F 17/00; G06F 17/60
(52) U.S. Cl. ............... 604/4.01; 604/403; 604/187; 604/189; 604/191; 128/923; 128/DIG. 6; 128/DIG. 22; 705/3; 706/924
(58) Field of Search .................. 604/4–6, 6.01, 604/187, 189, 191, 65, 67, 82, 403–404, 407; 607/59, 60, 63; 128/920, 923–24, DIG. 6, DIG. 22; 705/1–3; 706/45, 46, 52, 55, 924, 934; 714/100, 1, 25–26, 44, 46, 47, 48

(56) References Cited

U.S. PATENT DOCUMENTS

| | | | |
|---|---|---|---|
| 3,770,382 A | 11/1973 | Carter et al. ........... 23/253 R |
| 4,619,640 A | * 10/1986 | Potolsky et al. ............... 604/7 |
| 4,828,716 A | 5/1989 | McEwen et al. ............ 210/740 |
| 4,857,716 A | * 8/1989 | Gombrich et al. .......... 235/375 |
| 5,272,318 A | * 12/1993 | Gorman ..................... 235/375 |
| 5,383,858 A | * 1/1995 | Reilly et al. ............... 604/152 |
| 5,460,490 A | 10/1995 | Carr et al. .................. 417/44.2 |
| 5,593,390 A | * 1/1997 | Castellano et al. ......... 604/187 |
| 5,603,845 A | 2/1997 | Holm ......................... 210/782 |
| 5,605,541 A | 2/1997 | Holm ........................... 604/82 |
| 5,769,811 A | 6/1998 | Stacey et al. .................. 604/4 |
| 5,844,087 A | * 12/1998 | Zimmerman et al. ....... 530/381 |
| 5,954,700 A | * 9/1999 | Kovelman ................. 604/232 |
| 5,958,253 A | * 9/1999 | Holm ......................... 210/749 |
| 6,263,259 B1 | * 7/2001 | Bartur ........................ 700/240 |

* cited by examiner

*Primary Examiner*—Patricia Bianco
(74) *Attorney, Agent, or Firm*—John M. Kilcoyne

(57) ABSTRACT

The present invention provides methods and devices for maintaining the integrity of blood products throughout preparation, processing and application to a patient or desired site. Coding methods are incorporated onto or into processing and delivery containers which coding methods contain information identifying the donor and/or recipient. Additionally or alternatively the coding methods may contain information pertaining to a specific preparation or application process to be carried out. Blood product processors and blood product applicators include decoding methods to ensure the blood product is administered to the appropriate recipient and further that it has been prepared and applied according to desired processes.

3 Claims, 4 Drawing Sheets

BLOOD PRODUCT DELIVERY SYSTEM

This application claims priority to Ser. No. 60/053,746 filed Jul. 25, 1997.

WO 97/20585 describes an applicator useful for delivering a biological polymer, such as a surgical sealant, to a desired site. The system for sealant application includes one or more cartridges which contain components to form the sealant and maintain them separately until co-application so as not to form the sealant prematurely and block the applicator. The components within the cartridges are fed through tubing means to the applicator nozzle by motion of pistons within the cartridges. The piston movement which enables delivery of the sealant components is, in turn, provided by a automated applicator drive unit which includes electromechanical drive means responsive to an actuator means activated by the surgeon or user. Preferably, the applicator is remote from the automated applicator drive unit such that the surgeon does not have to hold the sources of sealant components in her hand, providing for the design of a smaller, easier-to-use applicator. In preferred embodiments the sealant components can be a fibrin monomer solution and a polymer-initiating buffer as taught in EP 592242, or can be a fibrinogen component and a thrombin or thrombin-like enzyme component. Most preferably, the sealant components are from a single donor and optimally are autologous to the patient receiving the sealant.

U.S. Pat. No. 5,603,845 describes a preparation unit which is a closed container having at least two chambers separated by a piston moveable between the chambers. Blood can be placed onto the first chamber of such a preparation unit and placed in a centrifuge to separate plasma from red blood cells. Plasma is thereupon transferred to the second chamber and subjected to a process which concentrates a desired blood component, e.g., fibrin monomer. A fibrin monomer solution is thereafter collected in a removable cartridge within the preparation unit which collects the fibrin monomer as described in EP 654669 and can thereafter be removed and placed into the automated application unit of the application system described in WO 97/20585. Again, single donor preparations, preferably autologous to the patient, are preferred. Other preparation units are disclosed in U.S. Pat. Nos. 5,738,784, 5,733,446.

Technology such as that described above provides a method of preparing and applying a single donor, or preferably autologous, sealant to a patient. To maintain the integrity and ensure the reliability of this valuable technology, a system or method which safeguards against the misapplication of such biological polymers, e.g., fibrin sealants, would be a useful addition to the art. Further, the preparation unit as used in the above described U.S. Pat. Nos. 5,603,845, 5,738,784, 5,733,446 is placed within a programmable centrifuge unit which may include different programs to process the blood in different ways. For example, blood can be processed to provide differing concentrations of fibrin monomer, components other than fibrin monomer, a platelet-rich or platelet-poor component, or a smaller volume, e.g., for pediatric use. Preparation units which are different sizes, of different configuration or pre-loaded with different reagents may be employed. It is incumbent upon the centrifuge operator to select the proper centrifuge program according to the desired end product and consistent with the particular preparation unit employed.

SUMMARY OF THE INVENTION

In accordance with the present invention a system for applying a single donor or autologous blood product to a patient comprises:

an applicator for applying the blood product;

an automated applicator drive unit in fluid communication with the applicator, which unit includes containers for components of the blood product, an electromechanical drive means to deliver the components to the applicator, wherein the drive means is responsive to a control means which is, in turn, responsive to an actuator means activated by the user;

coding means on the containers of components and on the patient which provides information identifying the desired donor and desired recipient of the components;

decoding means, connected to the control means, capable of blocking the application process if the information on the coding means of the patient does not correspond to the information in the coding means of the containers of the components.

In preferred embodiments the containers of components also serve as, or are a part of, the preparation unit used prior to the application process to prepare the components from the patient's blood.

Further, in accordance with the present invention, coding means are provided on a preparation unit or processing container for blood products so that a decoding means within the blood centrifuge or processor can read the code or the unit or container and automatically select the appropriate program or set of process steps for that particular unit or container.

DETAILED DESCRIPTION OF THE PREFERRED EMBODIMENTS

The present method and devices provides an added level of reliability to blood processing systems which are utilized to prepare and deliver single donor or autologous blood products to patients. This is critical in any setting involving such procedures and becomes especially important in situations where multiple patients are being treated daily, even simultaneously, such as in a surgical suite of a hospital when the blood products are, for example, surgical sealants. The present method and device provide this extra reliability and accuracy by ensuring that 1) the proper blood product is administered to the proper recipient or recipient site; and 2) the blood is processed in an accurate or desired manner, i.e., according to a desired process or set of process steps.

Figure 1:
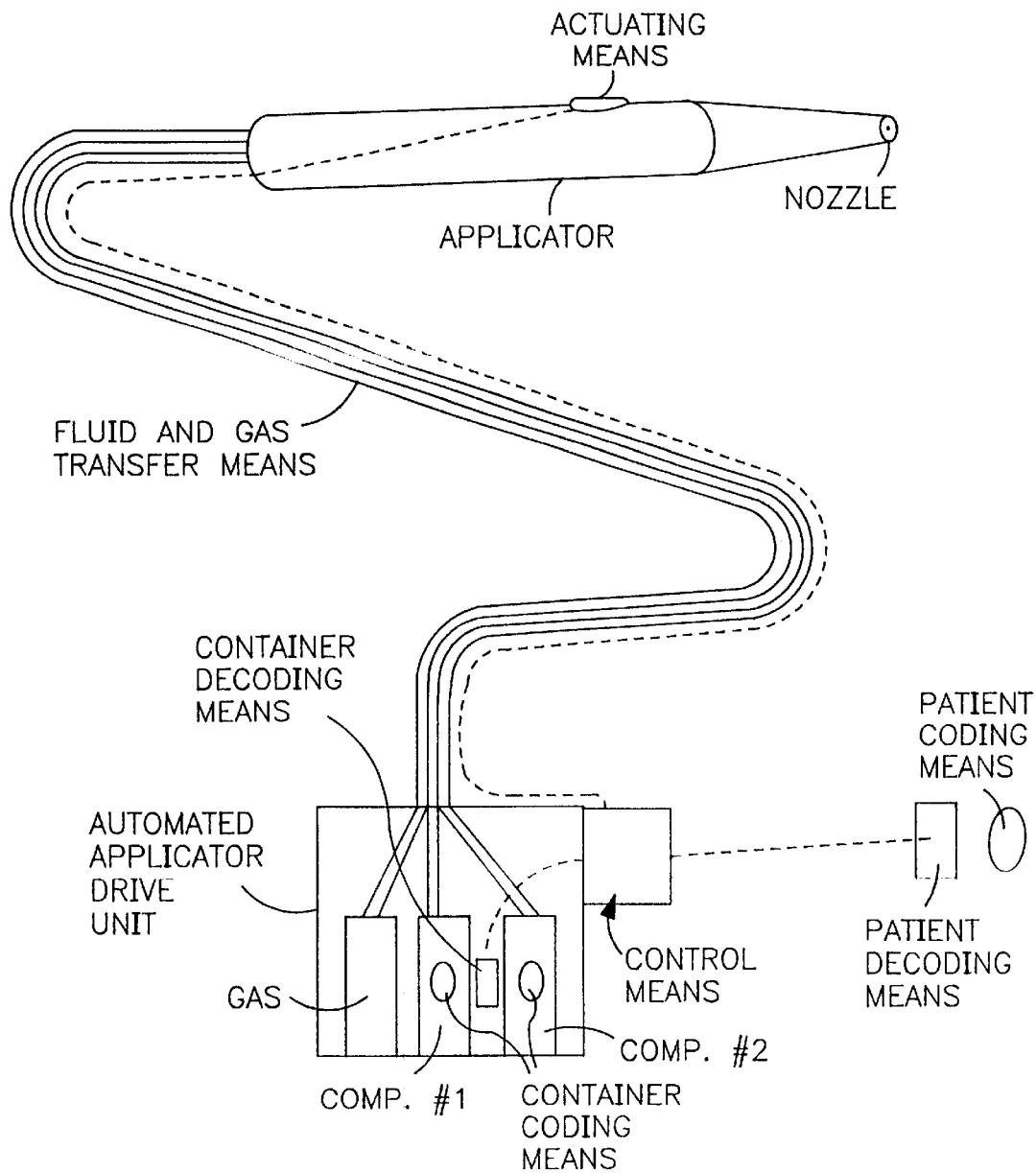
FIG. 1 illustrates an applicator system having coding and decoding means in accordance with the present invention.

FIG. 1 shows a basic diagram of the present invention as applied to a surgical sealant application system, e.g., a system for applying a fibrin sealant to a patient. The system is shown to have an automated applicator drive unit which contains sources, i.e. containers, of at least one component for forming the desired sealant. FIG. 1 illustrates two component containers and an optional gas source which can be utilized to facilitate spray delivery of the components. The automated applicator drive unit is in fluid communication with the applicator itself. It needs to be appreciated that any form of applicator can be utilized and that the applicator and drive unit, although preferably remote from each other, can be an integral unit. Dotted lines shows signal communication between the actuating means on the applicator and control means of the drive unit. The signal can be electrical or can be non-electrical as described in WO 97/20585 where the signal is differential air pressure, but can be any convenient means. In practice, the surgeon depresses the actuating means and the control means in response to the so-produced signal delivers components and/or gas from the containers, through the fluid/gas transfer means, to the applicator and out the nozzle for delivery to the desired site/ patient. Delivery of the components from the containers is accomplished by mechanical means to drive pistons into the component containers.

In accordance with the present invention such a system is further provided with coding means on one or both of the component containers and coding means on, or near, the patient. Coding means are indicated in FIG. 1 by the oval shapes. The coding means each contain matching information corresponding to the desired donor and desired recipient or patient. Of course for autologous delivery the donor and recipient are the same person. Although the recipient throughout this application is referred to as a patient, it should be noted that this system could also be used to ensure the proper deposition at any desired site, i.e., to create a medical implant or medical device or form a film intended for a specific patient or for a dressing, suture or prosthetic device intended for a specific patient. Decoding means (designated in FIG. 1 by the rectangles) are provided to read the information on one or both of the component containers and on the patient. These decoding means provide signals to the automated applicator drive unit and means are provided to make sealant application impossible if the information on the container(s) does not match the information on the patient. As shown in FIG. 1, the decoding means sends signals to the control means of the automated applicator drive unit, however these signals could be incorporated and processed elsewhere in the drive unit so as to provide the desired safeguard as would be apparent to those skilled in the art.

Figure 2:
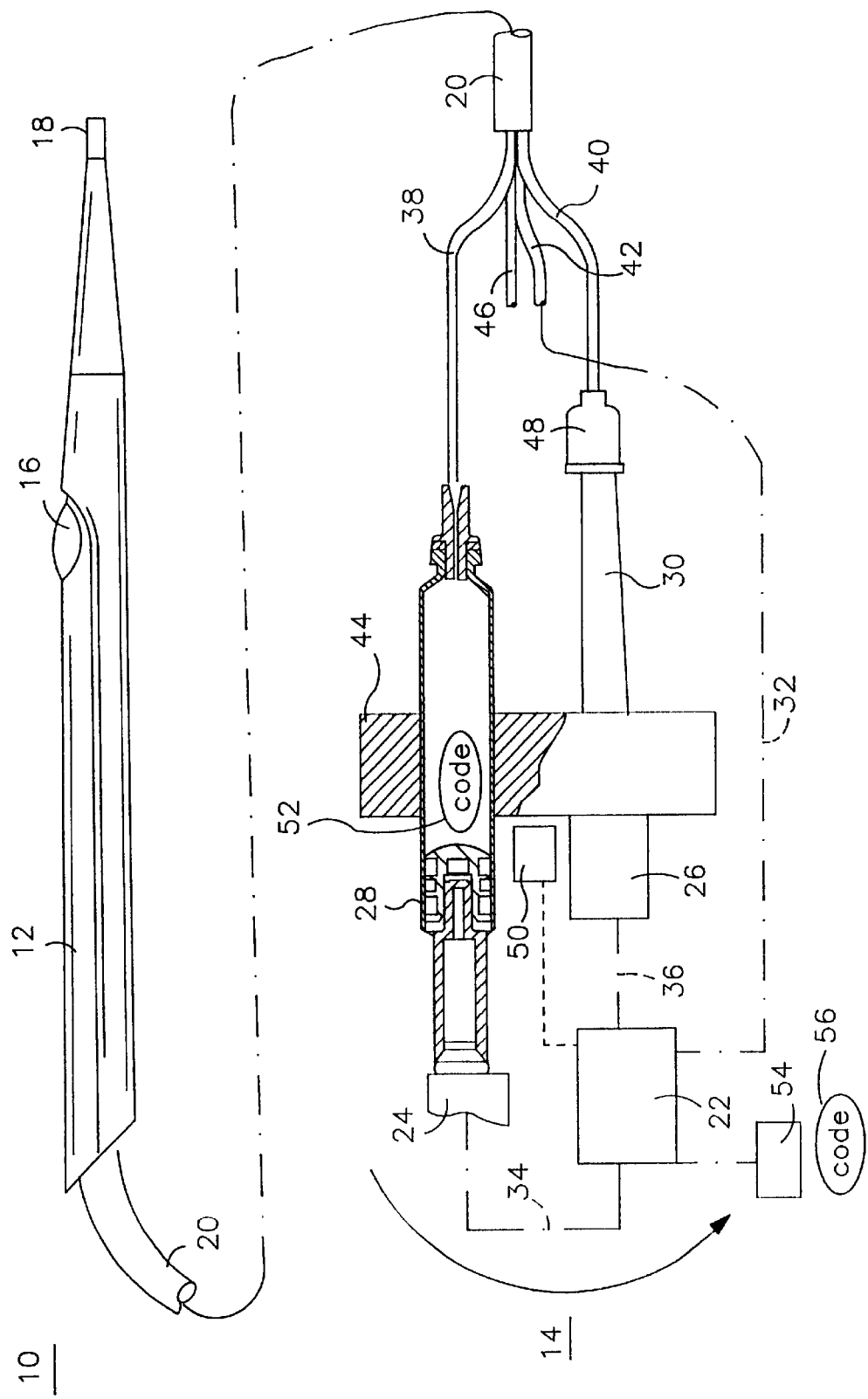
FIG. 2 shows an alternate applicator system having coding and decoding means in accordance with the present invention.

FIG. 2 provides another illustration of the an embodiment of the present invention wherein the application system is shown generally as 10, comprising an applicator 12 and an automated drive unit 14. The applicator 12 includes an actuating means 16 and a nozzle 18 and is in fluid communication with the drive unit, 14 via fluid transfer means 20. The drive unit 14 is shown to include a control means 22 which can activate component drive means 24 and gas drive means 26 so as to deliver a sealant compound from a component container 28 and gas from a gas nozzle 30. A signal from the actuator is communicated via actuator signal line 32 to control means 22 which is turn delivers "drive" or "off" signals to component drive means 24 and gas drive means 26 via control signal lines 34, 36, respectively. The fluid transfer means 20 comprises a component delivery tube 38, a gas delivery tube 40 and in this case an actuator tube 42 in communication with the actuator 16, although other actuator signal producing means can be employed. Component container 28 and gas nozzle 30 are held in position by a retainer means 44. Additional component containers can be added and connected, for example, to additional component delivery tube 46. Tubing connection 48 couples with the gas nozzle 30 to the gas delivery tube 40 and another coupling (not shown) is used to couple the component container 28 (shown in cross section) to the component delivery tube 38.

Further in FIG. 2 and in accordance with the present invention, a container decoding means 50 is shown as part of the drive unit 14 and capable of reading information on the container coding means 52. Also, a patient decoding means 54 is provided to read the patient coding means 56. Both decoding means are in signal communication with the control means 22 of the drive unit 14 so that application of the component to the patient will only occur if the information on each of the coding means 52, 56 match each other.

Also, in accordance with the present invention, the applicator drive unit may be capable of carrying out different application steps in applying the blood component, e.g., flow rates, mixing ratios with other components, etc. The coding means on the component cartridge may additionally or alternatively include information corresponding to the specific application parameters to be employed. In this case, the decoding means within the applicator drive unit would be in signal communication with the control means to ensure that the desired application parameters are utilized.

Figure 3:
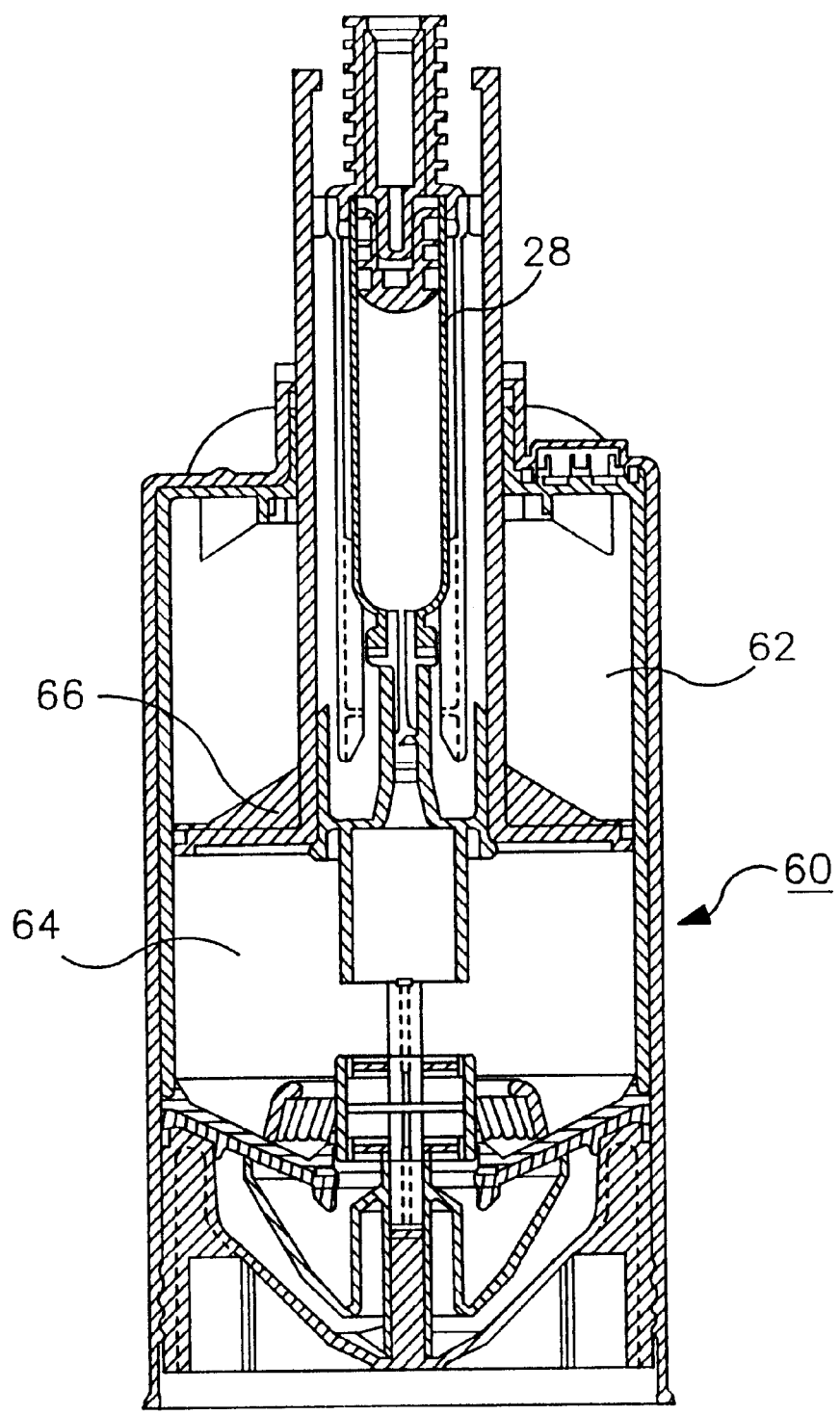
FIG. 3 illustrates a cross-sectional view of a preparation unit or processing container, including a component cartridge, useful in the present invention.

FIG. 3 shows a preparation unit as disclosed in U.S. Pat. Nos. 5,603,845, 5,738,784, 5,733,446 generally as 60. The details of this unit are described extensively in those published patent documents but basically the preparation unit has a first chamber 62 an a second chamber 64 separated by a piston 66. Blood is placed in the first chamber 62 and centrifuged so as to separate plasma and cellular components. Plasma is thereafter transferred to the second chamber 64 and processed to concentrate a desired blood component which is ultimately collected in component container 28. As can be seen by looking back at FIG. 2, component container 28 can thereafter be removed and placed into the automated applicator drive unit 14.

Figure 4:
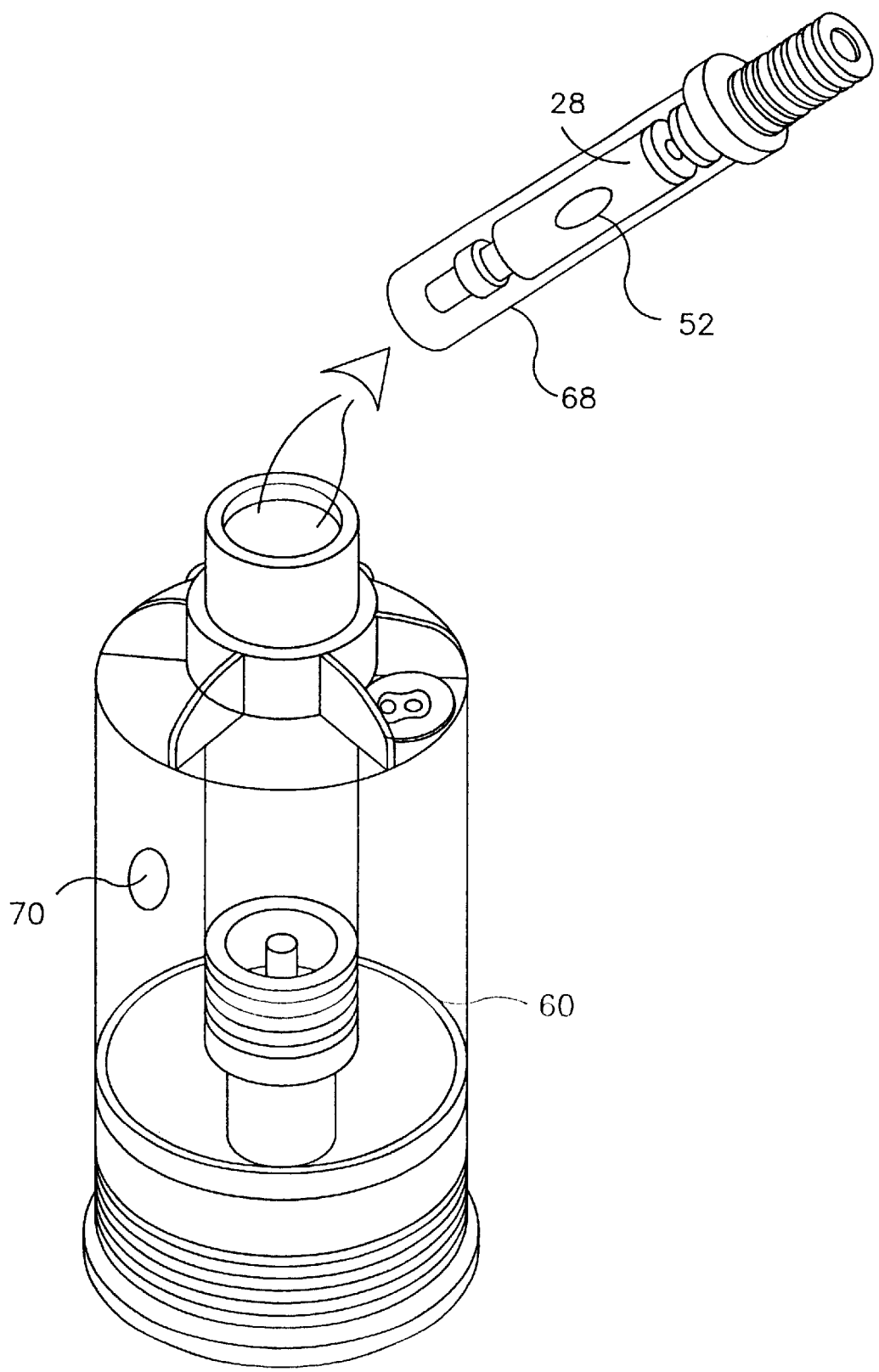
FIG. 4 shows a preparation unit and component cartridge having coding means in accordance with the present invention.

FIG. 4 further shows removal of component container 28 shown within a protective sleeve 68 from the preparation unit 60. FIG. 4 also shows, further in accordance with the present invention, that not only container coding means 52 but also preparation unit coding means 70 can be incorporated into the present system. In many cases blood will be taken directly from the donor, placed into the preparation unit 60 and processed in a processor or centrifuge unit (not shown). If the container coding means 52 cannot readily be scanned when the component container 28 is down within the preparation unit 60 as shown in FIG. 3 prior to processing, it may be useful to properly identify the correct blood-containing preparation unit 60 by way of the additional preparation unit coding means 70. Further, this becomes especially important if the blood is taken from a donor far enough ahead of processing or use so as to require temporary storage and/or transfer of location. In this instance the possibility of interchanging blood-containing preparation units increases and the preparation unit coding means 70 becomes critical. This could be used in conjunction with a decoding means (not shown) either within the centrifuge processor (not shown) into which the preparation unit 60 is placed for processing or with a free standing decoding means. In either case, the purpose is to ensure that information on the preparation unit coding means 52 corresponds to information on the patient coding means 56 so that the correct blood is retrieved from storage and/or processed at the right time. It should be appreciated that the component container 28 can be actually serve as the preparation unit in situations where the blood is to be stored and/or processed in the component container 28 itself without the need for a preparation unit.

Also, as mentioned above, an important aspect of the present invention involves the incorporation of a decoding means into a centrifuge or other blood processing apparatus. This would provide that the centrifuge or process operator could properly ascertain the identity of the donor and/or recipient. In a further embodiment, the coding means on the preparation unit and/or component cartridge could include information regarding the specific process to be performed. A centrifuge or blood processor capable of running various programs or processes could decode the coded information and ensure that the proper program was employed. This is useful in preparing, e.g., differing concentrations of fibrin monomer, alternative blood components, platelet-rich or platelet-poor compositions or any other blood product for which the preparation process can be programmed into the centrifuge or processor.

The present invention can be utilized in any instance where a specific blood product is intended for delivery to a specific patient and can be employed for virtually any blood products. Fibrin sealant application is preferred and discussed herein but the present invention should not be so limited. Preferred fibrin sealant systems would concurrently deliver a fibrin monomer component and a polymer-initiating buffer solution, preferably with a gas to provide spray mixing all of which are disclosed in WO 97/20585. In this case the fibrin monomer solution container (at least) would include a coding means. In systems which apply autologous or single-donor fibrinogen and thrombin components, each of the containers for these components would include a coding means. In each case the coding means information on the component would be checked against coding means on the patient.

This system is readily employed when a kit including the preparation unit (with component container), venepuncture set (for taking blood) and applicator is provided. Such a kit would include identical coding means on the preparation unit, the component container and one on, or with, the venepuncture kit for the patient (preferably a bracelet or similar tag). Decoding means, as described above, are used to compare the patient code to the preparation unit code to ensure that the proper blood is processed and/or to ensure that the proper process in employed and/or to compare the resulting blood product to the patient to ensure that the proper blood product is applied to the intended patient.

Coding and decoding means as described herein can refer to any system or technology for labeling articles with a form of identification and providing certain action in response to reading such identification. Bar coding/scanning technology, laser etching, magnetic coding or any other technologies available could be employed. Bar coding and laser etching are ideally suited for this purpose and are the preferred methods of carrying out this invention.

We claim:

1. An applicator system for delivering a processed blood product to a desired site or recipient comprising:

a container for containing the processed blood product, wherein said container is adaptable to be placed inside a blood processing system for processing single donor blood;

control means for initiating and controlling a specific process which is one of a plurality of processes programmed within the applicator system;

coding means on said container for including information which identifies a specific process to be employed with that container; and machine reading and decoding means in signal communication with said control means for machine reading and decoding information within said coding means and prompting said control means to select, initiate and control the specific process from said plurality of processes which corresponds to the information within said coding means; and an applicator in fluid communication with the container containing the processed blood product, said applicator being capable of delivering the processed blood product to a desired site or recipient, wherein said blood product is used to form a fibrin sealant.

2. The application system of claim 1 wherein said coding means further includes information corresponding to a single donor of said blood.

3. The application system of claim 1 wherein said coding means further includes information corresponding to said desired site or recipient.

* * * * *